United States Patent

Kluger et al.

[11] 4,313,004
[45] Jan. 26, 1982

[54] PROCESS FOR THE REDUCTION OF DICYANOGLYCOLS

[75] Inventors: Edward W. Kluger, Pauline; Andre M. Goineau, Spartanburg, both of S.C.

[73] Assignee: Milliken Research Corporation, Spartanburg, S.C.

[21] Appl. No.: 230,938

[22] Filed: Feb. 2, 1981

[51] Int. Cl.³ .............................................. C07C 85/12
[52] U.S. Cl. .................................. 564/491; 564/490; 564/493; 568/613; 568/675
[58] Field of Search .......................... 564/491, 490, 493

[56] References Cited

U.S. PATENT DOCUMENTS 2,584,970 2/1952 Alexander et al. ................. 564/491
3,331,877 7/1967 Smolin ................................ 564/491

FOREIGN PATENT DOCUMENTS 460099 10/1949 Canada ................................ 564/491
718461 9/1965 Canada ................................ 564/491
51-24484 7/1976 Japan .................................. 564/491
490922 5/1937 United Kingdom ................. 564/491

*Primary Examiner*—John Doll
*Attorney, Agent, or Firm*—H. William Petry; Terry T. Moyer

[57] ABSTRACT

A method for preparing a diaminoalkoxy compound of the formula:

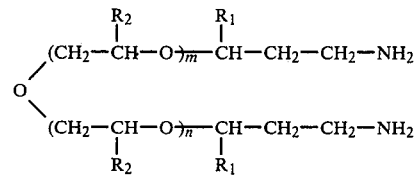

wherein m and n are both numbers from 0 to about 25 and m+n equals at least 1, $R_1$ is selected from H and a lower alkyl group having from 1 to about 4 carbon atoms; and $R_2$ is selected from H and an alkyl group containing from 1 to about 10 carbon atoms; which comprises incrementally introducing a dicyanoglycol compound of the formula:

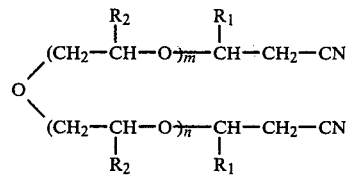

wherein m, n, $R_1$ and $R_2$ have the values indicated above into a reaction medium at a rate sufficient to minimize cleavage reactions, at a temperature of from about 90° C. to about 160° C. in the presence of hydrogen at a pressure of from about 800 psi to about 2200 psi; ammonia in an amount of from about 10 to about 40 weight percent based on the weight of dicyanoglycol compound; and a nickel catalyst in an amount sufficient to catalyze said reaction, whereby said dicyanoglycol compound is reduced to said diaminoalkoxy compound.

11 Claims, No Drawings

PROCESS FOR THE REDUCTION OF DICYANOGLYCOLS

The present invention relates to the catalytic hydrogenation of nitriles. More particularly the present invention relates to a process for the preparation of bis-(-3-aminopropyl) glycols by hydrogenation of bis-(-2-cyanoethyl) glycols.

Various techniques are known whereby primary, secondary and tertiary amines may be prepared by catalytic hydrogenation of the corresponding nitriles. It is also known that the presence of ammonia in the reaction medium may be effective in minimizing undesired coupling reactions during nitrile hydrogenation. Thus reductions in ammoniacal alcohol solutions have been recommended as the most suitable means for producing primary amines from a variety of nitriles.

It has also been reported that products of nitrile hydrogenation depend markedly on the catalyst and on whether the nitrile is aliphatic or aromatic. In this regard Russel, et al., J. Org. Chem. 37, 3552 (1972) report that nickel and nickel boride may be the best catalysts for converting low molecular weight aliphatic nitriles to primary amines. The yield has been reported to be nearly quantitative by reduction in ammoniacal methanol. Greenfield, H., Ind. Eng. Chem. Prod. Res. Dev. 6, 142 (1967).

Ordinarily dinitriles such as adiponitrile may be reduced to the corresponding amino compounds by the available batch or incremental hydrogenation modes without any substantial reported instances of adverse side reactions. Thus U.S. Pat. No. 2,449,036 to Greenfield reports a process for the manufacture of primary amines which involves the hydrogenation of nitriles, especially the nitriles of higher fatty acids in the liquid phase in the presence of nickel or cobalt catalyst and a strong base that is soluble in water.

U.S. Pat. No. 3,461,167 to Buehler discloses a process for the preparation of hexamethylenediamine by the hydrogenation of adiponitrile in the presence of ammonia and a hydrogenation catalyst wherein the hydrogenation is carried out in a series of reaction zones to reduce the amount of ammonia consumed. U.S. Pat. No. 3,821,305 to Bartalini, et al. teaches a process for hydrogenation of adiponitrile in the liquid phase to hexamethylenediamine wherein the proportions of catalyst, water and caustic alkali are closely controlled to improve yield and product quality by supplying those substances in amounts corresponding to those removed from the reaction vessel.

The hydrogenation of cyanoalkylated glycols, however, especially on a commercial scale using the known and available techniques has been typically accompanied by a variety of undesired side reactions which have adversely affected both yield and purity of the amine product. Specifically, it has been observed that such cyanoalkylated glycols may undergo exhaustive cleavage to form relatively large and undesired amounts of glycols, amino alcohols, polyamines and polymeric impurities as well as the diaminoglycol in ordinary batch-type reductions with Raney nickel catalysts. See O. F. Wiedeman, et al., "Some Amine Derivatives of Acrylonitrile" J.A.C.S., Vol. 67, p. 1994-1996; see also U.S. Pat. No. 3,377,383 to Farkas, et al., (Air Products) where certain undesired side reactions are described and a process is suggested whereby such side reactions may be minimized by carrying out the reaction at a low temperature.

Attempts have also been made to avoid undesired side reactions in the preparation of certain cyanoalkylated glycols normally associated with the use of a conventional Raney nickel catalyst by using other catalyst systems such as cobalt, palladium, platinum, ruthenium and rhodium (see, e.g., Decker, et al., 1,4-bis(3-aminopropoxy)butane, C.A. 78:11934n where hydrogenation is accomplished continuously over a cobalt catalyst in the presence of $H_3PO_4$). Unfortunately, however, the cost of such catalysts in a commercial process to reduce cyanoalkylated glycols is unattractive to say the least, and perhaps even prohibitive, especially since the catalyst recycle may be questionable which is the situation as to known hydrogenation techniques. (See, for instance, U.S. Pat. No. 4,216,169 where it is reported that certain nickel and cobalt catalysts lack the long life required in a commercial process.)

Accordingly, it would be highly desirable to provide a process whereby dicyanoglycols may be successfully reduced to the corresponding diaminoalkoxy compounds in high yields and with minimal formation of undesired bi-products using a relatively inexpensive nickel catalyst system.

According to the present invention, a method is provided for preparing a diaminoalkoxy

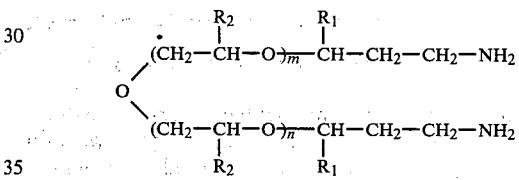

wherein m and n are both numbers from 0 to about 25 and m+n equals at least 1, $R_1$ is selected from H and a lower alkyl group having from 1 to about 4 carbon atoms; and $R_2$ is selected from H and an alkyl group containing from 1 to about 10 carbon atoms; which comprises incrementally introducing a dicyanoglycol compound of the formula:

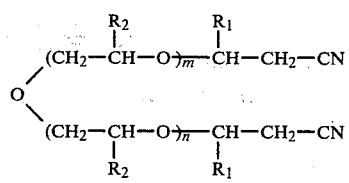

wherein m, n, $R_1$ and $R_2$ have the values indicated above into a reaction medium at a rate sufficient to minimize cleavage reactions, at a temperature of from about 90° C. to about 160° C. in the presence of hydrogen at a pressure of from about 800 psi to about 2200 psi; ammonia in an amount of from about 10 to about 40 weight percent based on the weight of dicyanoglycol compound; and a nickel catalyst in an amount sufficient to catalyze said reaction, whereby said dicyanoglycol compound is reduced to said diaminoalkoxy compound. Preferably in the above formulas $R_2$ is selected from H and a lower alkyl group containing from 1 to about 4 carbon atoms. The values for m and n are both preferably at least 1 and not more than about 10. $R_1$ is preferably H. The most preferred embodiment of the present invention involves application of the process to the compound bis-(-2-cyanoethyl)-diethyleneglycol to provide the product compound bis-(-3-aminopropyl)diethyleneglycol.

A preferred embodiment of the present invention will be described with particular reference to a preferred product compound bis-(-3-aminopropyl)glycol and a preferred starting material bis-(-2-cyanoethyl)glycol, although it is to be understood that the invention is not to be limited thereby. In accordance with this preferred embodiment, bis-(-3-aminopropyl)glycol is produced by the incremental addition and reduction of bis-(-2-cyanoethyl)glycols into a reaction vessel containing hydrogen, ammonia, either in the presence or absence of a solvent and a Raney nickel catalyst. The corresponding diaminoglycol is produced in high yield as shown in the equation below:

EQUATION I
Incremental Addition and Reduction Mode

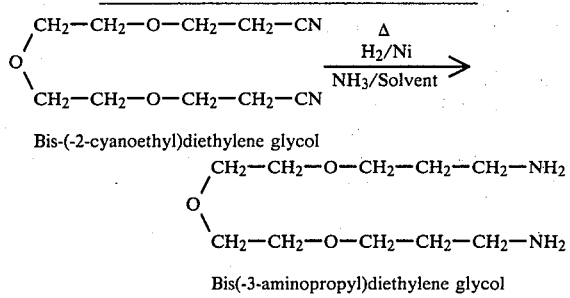

Bis-(-2-cyanoethyl)diethylene glycol

Bis(-3-aminopropyl)diethylene glycol

As noted above, conventional batch-type procedures which have heretofore been employed for the reduction of cyanoalkylated glycols have resulted in generally undesirable low yields with undesired by-product formation resulting from cleavage side reactions. These reactions which are typical in batch-type techniques are shown in Equation II below.

EQUATION II
Batch-type Reduction Mode
Showing Cleavage Side Reactions

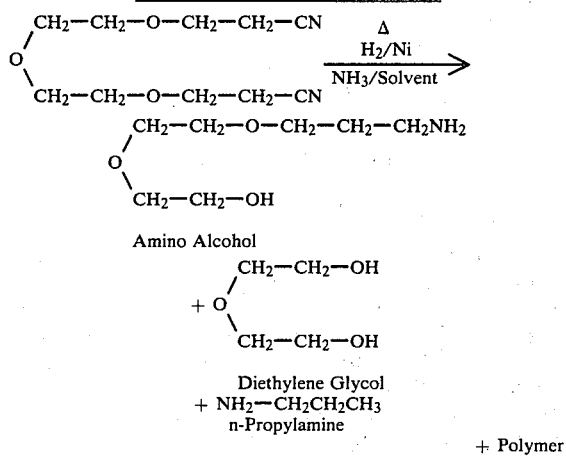

Amino Alcohol

Diethylene Glycol
+ $NH_2-CH_2CH_2CH_3$
n-Propylamine

+ Polymer

The amount of exhaustive cleavage that may occur in ordinary batch reductions of cyanoethylated glycols can vary generally from about 30-80 weight percent depending upon the amount of catalyst loading, the hydrogen pressure, the reaction temperature, the pH of the mixture, e.g., depending upon the presence of caustic, and whether or not a solvent is being used.

In addition to exhaustive cleavage, ordinary batch reductions of cyanoethylated glycols may lead to products with dark colors and polymer present. Both the dark color and presence of polymer are a disadvantage in the final product. Also, polymer formation leads to catalyst recycling problems which may make the batch mode even more commercially unattractive. Thus, U.S. Pat. No. 4,216,169 (Table II, Nos. 28 and 29) teaches certain catalyst recycle problems for both nickel and cobalt catalysts in reduction of dinitriles even in a continuous mode hydrogenation.

In contrast to ordinary batch reduction modes of dicyanoethylated glycols, the method of the present invention may provide diaminoglycols without any substantial exhaustive cleavage side reactions and catalyst deactivation. Generally, purities in the range of about 95-99 percent diaminoglycol and catalyst recycles of at least seven are obtainable experimentally according to the process of the present invention.

The temperature at which the above described incremental reduction of dicyanoethylated glycol is carried out can vary widely. However, generally, the temperature will be within a range of from about 90°-150° C. and preferably in the range of about 120°-135° C. Likewise, the period of time required for the reaction to go to substantial completion can vary widely, such being dependent on the hydrogen pressure and the particular nickel catalyst employed as well as the temperature at which such reaction is carried out. Generally, however, the reaction proceeds to completion when the reactants are contacted at the required temperature in a matter of seconds. Pressures in the range of about 1000 to about 5000 psi can be used to accomplish the reduction. While pressure in the higher range (2100-5000 psi) can be used and may be advantageous, the preferable range of pressure is 1000-2000 psi.

The use of ammonia in this reduction is employed in the process to maintain high yields of the corresponding diaminoglycol. The presence of ammonia serves to inhibit formation of secondary amines. The amount of ammonia used may vary from about 5 moles of ammonia per mole of dicyanoglycol to 30 moles per mole of dicyanoglycol. Preferably about 12 to about 20 moles of ammonia are used per mole of dicyanoglycol.

The hydrogenation of the dicyanoglycol may be carried out in the presence or absence of a solvent. When solvent is employed, any suitable solvent which will not interfere with the desired hydrogenation can be employed, such as cycloaliphatic ethers, e.g., dioxane, tetrahydrofuran, and the like, and higher boiling hydrocarbons, e.g., hexane, cyclohexane, heptane, decane, toluene, xylenes, and the like and alcohols, e.g., methyl alcohol, ethyl alcohol, isopropyl alcohol, isobutyl alcohol and the like. In addition the nickel catalyst can be slurried with the desired diaminoglycol prior to incremental addition and reduction of the dicyanoglycol.

In carrying out the reduction of the dicyanoglycol any suitable nickel reduction catalyst can be employed. Typical of such reduction catalysts are Raney number 28 nickel, and Raney nickel promoted either by chromium or molybdenum including salts and oxides thereof and the like. Further, such catalysts can be in their free metal state or extended on a support such as charcoal, aluminum, kieselguhr and the like. The amount of catalyst employed in the reduction can vary widely. However, generally the amount of catalyst will vary from about 1 to 30 weight percent, preferably from about 5 to 10 weight percent.

According to the invention the dicyanoglycol may be added incrementally to the reduction mixture at a rate sufficient to minimize exhaustion cleavage reactions. In addition the reaction medium should be maintained at the required pressure, temperature, and catalyst loading in order to avoid exhaustive cleavage as described in Equation II. The dinitrile incremental addition rate may vary greatly depending on the catalyst loading, reaction pressure, reaction temperature and reactor size in which the hydrogenation process occurs. Generally, the addition rate should be adjusted so that the reduction process is substantially instantaneous. Furthermore, according to the invention the reaction medium generally should not contain any more than about 5 percent reaction intermediates, or more preferably less than about 2 percent reaction intermediates as measured by GLC to minimize or eliminate undesirable results.

One particularly important use for the compounds produced by the process of the present invention is their use as epoxy curing agents for polyepoxides. The polyepoxides which can be cured at elevated temperatures using the amino compounds as herein described are those polyepoxides possessing at least two

groups. These groups may be terminal, i.e.,

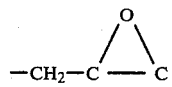

groups, or they may be in an internal position. However, especially desirable results can be obtained when the epoxy groups are terminal. The polyepoxides may be saturated or unsaturated, aliphatic, cycloaliphatic, aromatic or heterocyclic, and may be substituted such as with hydroxyl groups, ether radicals and the like. Further, the polyepoxides can be monomeric or polymeric. Such polyepoxides, and their preparation, are well known in the art.

The curing of the polyepoxides with the above-described amino compound curing agents of the present invention may be accomplished by simply mixing the two components together. While the reaction between the two components may occur slowly at room temperature, improved results can be obtained if the mixture is heated to a temperature of from about 50° C. to about 280° C. for a period of time of from about 1 to about 12 hours and thereafter post-curing the reaction product for an additional period of time from about 1 to about 8 hours at a temperature of from about 140° C. to about 225° C. With a small casting, curing of the reaction mixture can be obtained by heating the reaction mixture for about 2 hours at a temperature of from about 80° C. to about 100° C. and thereafter post-curing the reaction product at a temperature of from about 140° C. to about 225° C. for an additional 2 hours or so.

In curing polyepoxides it is generally desirable that the polyepoxide be in a mobile condition when the curing agent is added to ensure uniform mixing. If the polyepoxide is extremely viscous or solid at room or casting temperature, the polyepoxide may be heated to reduce the viscosity or a volatile liquid solvent which can escape from the polyepoxide composition containing the novel amino compound curing agent by evaporation before and/or during the curing of such polyepoxide composition can be added to the polyepoxide to reduce its viscosity. Typical of such volatile liquid solvents are ketones, such as acetone, methyl ethyl ketone and the like, ethers, such as ethyl acetate, butyl acetate and the like, ether alcohols, such as methyl, ethyl or butyl ethers of ethylene glycol and chlorinated hydrocarbons, such as chloroform.

In addition to the use of the amino compounds of the present invention as epoxy curing agents, many other uses can readily be envisioned by those skilled in the art. Thus, not only do the compounds of the present invention find utility as epoxy curing agents but such compositions can be employed as oil and fuel adductive intermediates. Further, the polyamines may be employed for the formation of diisocyanate compositions for the incorporation into polyurethane compositions, and the compound may be further reacted to form novel and useful polyamides.

In order to more fully describe the preparation and use of the novel compounds of the present invention the following examples are given. However, such examples are presented for illustration only and are not to be construed as unduly limiting the scope of the present invention. Unless otherwise indicated, all parts and/or percentages given in these examples are by weight.

EXAMPLE 1

In a 5000 cc three necked flask equipped with an overhead stirrer, reflux condenser, nitrogen purge, dropping funnel and thermometer was charged 1978.1 gm. (18.64 moles) of diethylene glycol and 3.0 gm. of anhydrous lithium hydroxide. The overhead stirrer was then adjusted to high speed. Acrylonitrile was then added through the dropping funnel. Over the course of 5 hours a total of 2880 cc of acrylonitrile was added and reaction temperature reached a maximum of 66° C. with a water bath being maintained above 52° C. The reaction flask was then post-heated at 52°–72° C. for an additional 40 minutes. The reaction contents were cooled to room temperature and neutralized with glacial acetic acid. The reaction contents were filtered and the crude reaction product was stripped of all excess acrylonitrile under vacuum (15–30 mmHg) at a temperature not exceeding 60° C. to give the liquid bis-(-2-cyanoethyl)diethylene glycol. A GLC analysis showed the product to contain 99 percent dicyanoglycol and about 1 percent monocyanoglycol. This dicyanoglycol was used without further purification.

EXAMPLE 2

In a two liter stirred autoclave was charged 400 gm. of bis-(-2-cyanoethyl)diethylene glycol, 522 gm. of isopropyl alcohol, and 150 gm. of wet Raney Number 28 nickel catalyst (~275 gm. on an absolute nickel basis). The autoclave was sealed and pressure checked to 2000 psi with hydrogen gas for leaks. Afterwards, 250 gm. of liquid ammonia was charged. The pressure was then adjusted to 400 psi with hydrogen gas and the autoclave was heated. On heating, an initial exotherm of about 30° C. occurred with full cooling water on and a pressure of 1600–1700 psi developed. The temperature was then adjusted to 125°–130° C. Samples were pulled from the autoclave and were analyzed by GLC until the reaction was near completion. After 45 minutes at 125°–130° C., the reaction was post-heated at 145°–150° C. for an additional 30 minutes. The autoclave was then cooled down and the contents were emptied. The excess ammonia and n-propylamine were removed from the crude product. A GLC analysis of the final product showed it to contain 25.5 percent of the aminoalcohol, 0.8 percent of reaction intermediates, 1.7 percent of high boilers and only 69.5 percent of the desired bis-(-3-aminopropyl)diethylene glycol, indicating that exhaustive cleavage had occurred during the batch reduction process.

EXAMPLE 3

In a two liter stirred autoclave was charged 400 cc of toluene and 80 gm. of wet Raney number 28 nickel catalyst (~40 gm. on an absolute nickel basis) which had been adjusted to 11.5–12.0 pH with 0.5 percent sodium hydroxide solution. The autoclave was sealed and pressure checked to 2000 psi with hydrogen gas for leaks. Afterwards 260 gm. of liquid ammonia was charged. The pressure was then adjusted to 400 psi with hydrogen gas and the autoclave was heated to 130°–135° C. where a pressure of 1650 to 1700 psi developed. The autoclave stirring rate was adjusted to 1735 rpm. The bis-(-2-cyanoethyl)diethylene glycol was pumped into the autoclave at a rate of 4.5–5.0 gm. per minute. Samples were pulled from the reactor and analyzed by GLC during the reduction process to ensure that no excessive amount of dinitrile or reaction intermediates built up (generally below 1.5 percent reaction intermediates and dinitrile were observed by GLC). After about 2½ hours about 600 gm. of dicyanoglycol had been pumped into the reactor. The pump was then turned off and the reactor was post-heated for an additional 30 minutes at 145°–150° C. The autoclave was then cooled down and the contents were emptied. The excess ammonia was removed from the crude products. A GLC analysis of the final product showed it to contain 0.1 percent of aminoalcohol glycol, 1.2 percent reaction intermediates, 1.4 percent of high boilers, and 97.6 percent of the desired bis-(-3-aminopropyl)diethylene glycol, indicating that practically no cleavage occurred during the incremental addition and reduction process.

EXAMPLE 4

Table 1 summarizes the experimental data for Raney nickel number 28, cycles 1–3. In a two liter stirred autoclave was charged 400 cc of toluene and 80 gm. of wet Raney number 28 nickel catalyst (~40 gm. on an absolute nickel basis). The three reactions were run according to the procedure followed in Example 3 except that about one-third of the crude reaction mixture was left in the reactor as a heel in place of the 400 cc of toluene on the second and third catalyst cycles. The reaction temperature, pressure, ammonia weight and caustic weight, as well as the rpm is included in Table 1 given below.

TABLE 1

| | | | | | 0.5% | COMPOSITION OF PRODUCT | | | |
|---|---|---|---|---|---|---|---|---|---|
| | | | RXN. | | | | | | |
| | | RXN. TEMP. | PRESSURE | NH$_3$ | NaOH | % | % | % HIGH | % RXN. |
| ENTRY | CYCLE | (°C.) | (PSI) | (GM) | (GM) | MONO | DIAMINE | BOILER | INT. |
| 1 | 1$^B$ | 135–140 | 1450–1700 | 330 | — | 0.7 | 96.8 | 0.7 | 1.6 |
| 2 | 2 | 135–140 | 1400–1700 | 230 | 30 | 1.8 | 96.0 | 1.0 | 1.2 |
| 3 | 3 | 135–145 | 1450–1800 | 230 | 30 | 2.4 | 93.0 | 2.0 | 1.8 |

CATALYST CYCLE FOR INCREMENTAL ADDITION AND REDUCTION OF BIS-(-2-CYANOETHYL)DIETHYLENE GLYCOL$^{A, C, D, E}$ $^A$1200 rpm
$^B$80 gm. wet Ni-28 charged + 400 cc of toluene
$^C$5–10% wt. loss of catalyst between cycles
$^D$About ⅓ of product mixture left in autoclave as heel between runs
$^E$Reaction was post-heated at 145–155° C. for 30 min. after addition of all dinitrile Entries 1–3 of Table 1 clearly show that high purity bis-(-3-aminopropyl)diethylene glycol and catalyst recycle are readily obtainable with our incremental addition and reduction process.

EXAMPLE 5

Table 2 summarizes the experimental data for Raney nickel number 28 cycles 1–7. In a two liter stirred autoclave was charged 400 cc of toluene and 80 gm. of wet Raney nickel number 28 catalyst (~40 gm on an absolute nickel basis). The seven reactions were run as in Example 4 except that 400 cc of toluene and 16 gm. of wet nickel number 28 catalyst make up (2 percent wet on the weight of the dinitrile) was charged after removing the crude reaction product in the second through sixth catalyst cycles. The reaction temperature, pressure, ammonia weight, and caustic weight as well as the rpm is included in Table 2 given below.

TABLE 2

CATALYST CYCLES (WITH ADD CATALYST) FOR INCREMENTAL ADDITION AND REDUCTION OF BIS-(-2-CYANOETHYL)DIETHYLENE GLYCOL$^{A, D, E, F}$

| | | | RXN. | | 0.5% | COMPOSITION OF PRODUCT | | | |
|---|---|---|---|---|---|---|---|---|---|
| | | RXN.TEMP. | PRESSURE | NH$_3$ | NaOH | % | % | % HIGH | % RXN. |
| ENTRY | CYCLE | (°C.) | (PSI) | (GM) | (GM) | MONO | DIAMINE | BOILER | INT. |
| 1 | 1$^B$ | 135–140 | 1650 | 270 | 20 | 3.6 | 95.3 | 0.2 | 0.9 |
| 2 | 2$^C$ | 140–145 | 1650 | 270 | 40 | 2.2 | 96.5 | 0.9 | 0.8 |
| 3 | 3$^C$ | 140–145 | 1110–1700 | 270 | 40 | 2.1 | 95.5 | 0.9 | 1.1 |
| 4 | 4$^C$ | 140–145 | 1650–1700 | 270 | 40 | 1.7 | 96.3 | 0.5 | 1.1 |
| 5 | 5$^C$ | 140–145 | 1650 | 270 | 40 | 1.2 | 96.8 | 1.0 | 0.8 |
| 6 | 6$^C$ | 140–145 | 1700 | 270 | 40 | 1.3 | 96.0 | 1.4 | 1.0 |

TABLE 2-continued

CATALYST CYCLES (WITH ADD CATALYST) FOR INCREMENTAL ADDITION AND REDUCTION OF BIS-(-2-CYANOETHYL)DIETHYLENE GLYCOL[A, D, E, F]

| ENTRY | CYCLE | RXN.TEMP. (°C.) | RXN. PRESSURE (PSI) | NH$_3$ (GM) | 0.5% NaOH (GM) | COMPOSITION OF PRODUCT | | | |
|---|---|---|---|---|---|---|---|---|---|
| | | | | | | % MONO | % DIAMINE | % HIGH BOILER | % RXN. INT. |
| 7 | 7 | 140–145 | 1700 | 270 | 40 | 3.6 | 94.9 | 0.8 | 0.6 |

[A] 1200 rpm
[B] 80 gm. wet Ni-28 + 400 cc of toluene charged
[C] 400 cc of toluene + 16 gm. of Ni-28 wet (2% on wt. of dinitrile)
[D] ~5% wt. loss between cycles of nickel catalyst
[E] About ⅛ of product left in autoclave between runs
[F] Reaction was post-heated at 145-155° C. for 30 min. after addition of all Entries 1–7 of Table 2 clearly show that high purity bis-(-3-aminopropyl)diethylene glycol and catalyst recycle are readily obtainable with our incremental addition and reduction process.

EXAMPLE 6

In a two liter stirred autoclave was charged 400 cc of toluene and 80 gm. of wet Raney-chromium promoted catalyst number 2400 (~40 gm. on an absolute metal basis) which had a pH of about 12.0 to 12.5. The autoclave was sealed and pressure checked to 2000 psi with hydrogen gas for leaks. Afterwards, 300 gm. of liquid ammonia was charged. The pressure was then adjusted to 400 psi with hydrogen gas and the autoclave was heated to 110°-115° C. where a pressure of 1650-1680 psi developed. The autoclave stirring rate was adjusted to 800-950 rpm. The bis-(-2-cyanoethyl)diethylene glycol was pumped into the autoclave at a rate of 4.5 to 5.0 gm. per minute. Samples were pulled from the reactor and analyzed by GLC during the reduction process to ensure that no excessive amount of dinitrile or reaction intermediates built up (generally below 1.5 percent reaction intermediates and dinitrile were observed by GLC). After about 2½ hours about 600 gm. of dicyanoglycol had been pumped into the reactor. The pump was then turned off and the reactor was post-heated for an additional 30 minutes at 145°-150° C. The autoclave was then cooled down and the contents were emptied. The excess ammonia was removed from the crude product. A GLC analysis of the final product showed it to contain 1.6 percent of aminoalcohol glycol, 1.6 percent of reaction intermediates, 1.4 percent of high boilers and 95.2 percent of the desired bis-(-3-aminopropyl)-diethylene glycol indicating that only a very small amount of cleavage occurred during the incremental reduction.

EXAMPLE 7

In a two liter stirred autoclave was charged 400 cc of toluene and 80 gm. of wet Raney-molybdenum promoted catalyst number 3000 (~40 gm. in an absolute metal basis) which had been adjusted to 11.5-12.0 pH with 0.5 percent sodium hydroxide solution. The autoclave was sealed and pressure checked to 2000 psi with hydrogen gas for leaks. Afterwards 300 gm. of liquid ammonia was charged. The pressure was then adjusted to 400 psi with hydrogen gas and the autoclave was heated to 110°-115° C. where a pressure of 1650-1680 psi developed. The autoclave stirring rate was adjusted to 800-950 rpm. The bis-(-2-cyanoethyl)-diethylene glycol was pumped into the autoclave at a rate of 4.5-5.0 gm. per minute. Samples were pulled from the reactor and analyzed by GLC during the reduction process to ensure that no excessive amount of dinitrile or reaction intermediates built up (generally below 1.5 percent reaction intermediates and dinitrile were observed by GLC). After about 2½ hours, about 600 gm. of dicyanoglycol had been pumped into the reactor. The pump was then turned off and the reactor was post-heated for an additional 30 minutes at 145°-150° C. The autoclave was then cooled down and the contents were emptied. The excess ammonia was removed from the crude product. A GLC analysis of the final product showed it to contain 0.9 percent of aminoalcohol glycol, 2.0 percent of reaction intermediates, 1.8 percent high boilers, and 95.2 percent of the desired bis-(-3-aminopropyl)diethylene glycol indicating that very little cleavage occurred during the incremental reduction.

EXAMPLE 8

In a two liter stirred autoclave was charged 400 cc of toluene and 80 gm. of wet Raney-nickel number 28 catalyst (~40 gm. of an absolute nickel basis) which had been adjusted to 11.5-12.0 pH with 0.5 percent sodium hydroxide solution. The autoclave was sealed and pressure checked to 2000 psi with hydrogen gas for leaks. Afterwards, 300 gm. of liquid ammonia was charged. The pressure was then adjusted to 400 psi with hydrogen gas and the autoclave was heated to 130°-135° C. where a pressure of 1650-1670 psi developed. The autoclave stirring rate was adjusted to 800-1000 rpm. Bis-(-2-cyanoethyl)ethylene glycol was pumped into the autoclave at a rate of 4.5-5.0 gm. per minute. Samples were pulled from the reactor and analyzed by GLC during the reduction process to ensure that no excessive amount of dinitrile or reaction intermediates built up (generally below 1.5 percent reaction intermediates and dinitrile were observed by GLC) after about 2½ hours about 600 gm. of dicyanoglycol had been pumped into the reactor. The pump was then turned off and the reactor was post-heated for an additional 30 minutes at 145°-150° C. The autoclave was then cooled down and the contents were emptied. The excess ammonia was removed from the crude product. A GLC analysis of the final product showed it to contain 0.8 percent aminoalcohol glycol, 0.5 percent reaction intermediates, 2.0 percent high boilers, and 96.8 percent of the desired bis-(-3-aminopropyl)ethylene glycol indicating that very little cleavage occurred during the incremental addition and reduction process.

EXAMPLE 9

In a two liter stirred autoclave was charged 400 cc of toluene and 80 gm. of wet Raney-nickel number 28 catalyst (~40 gm. on an absolute nickel basis) which had been adjusted to 11.5 to 12.0 pH with 0.5 percent sodium hydroxide solution. The autoclave was sealed and pressure checked to 2000 psi with hydrogen gas for leaks. Afterwards, 300 gm. of liquid ammonia was charged. The pressure was then adjusted to 400 psi with hydrogen gas and the autoclave was heated to 120°–130° C. where a pressure of 1600–1680 psi developed. The autoclave stirring rate was adjusted to 1200 rpm. Bis-(-2-cyanoethyl)ether was pumped into the autoclave at a rate of 4.5–5.0 gm. per minute. Samples were pulled from the reactor and were analyzed by GLC during the reduction process to ensure that no excessive amount of reaction intermediates built up (generally below 1.5 percent reaction intermediates and dinitrile were observed by GLC). After about 2½ hours about 600 gm. of dinitrile had been pumped into the reactor. The pump was then turned off and the reactor was post-heated for an additional 30 minutes at 145°–150° C. The autoclave was then cooled down and the contents were emptied. The excess ammonia was removed from the crude product. A GLC analysis of the final product showed it to contain 1.0 percent aminoalcohol glycol, 0.6 percent reaction intermediates, 2.4 percent high boilers, and 96.0 percent of the desired bis-(-3-aminopropyl)ether indicating that very little cleavage occurred during the incremental addition and reduction process.

The above examples clearly indicate the novel incremental addition and reduction process for dicyanoglycols. Furthermore, Examples 4 and 5 show that no catalyst recycling problems result in the use of Raney nickel in this process.

The incremental addition and reduction process for dicyanoglycols (Examples 3 through 9) is compared to an ordinary batch reduction in Example 2. Clearly, excessive cleavage of the dicyanoglycol has occurred in the batch reduction (Example 2) resulting in 25.5 percent of the monoaminoalcohol glycol. In all the experimental work with the incremental addition and reduction of dicyanoglycols (see Examples 3 through 9), no excessive cleavage was observed. In fact, the highest amount of monoaminoalcohol glycol was only 2.4 percent even with ½ the catalyst loading used in the batch reduction and in up to seven catalyst recycles.

What is claimed is:

1. A method for preparing a diaminoalkoxy

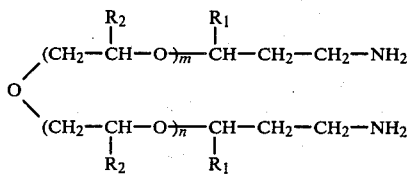

wherein m and n are both numbers from 0 to about 25 and m+n equals at least 1 $R_1$ is selected from H and a lower alkyl group having from 1 to about 4 carbon atoms; and $R_2$ is selected from H and an alkyl group containing from 1 to about 10 carbon atoms; which comprises incrementally introducing a dicyanoglycol compound of the formula:

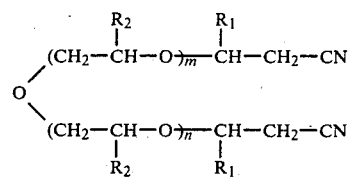

wherein m, n, $R_1$ and $R_2$ have the values indicated above into a reaction medium at a rate sufficient to minimize cleavage reactions, at a temperature of from about 90° C. to about 160° C. in the presence of hydrogen at a pressure of from about 800 psi to about 2200 psi; ammonia in an amount of from about 10 to about 40 weight percent based on the weight of dicyanoglycol compound; and a nickel catalyst in an amount sufficient to catalyze said reaction, whereby said dicyanoglycol compound is reduced to said diaminoalkoxy compound.

2. The method of claim 1, wherein said rate of incremental introduction of said dicyanoglycol into said reaction medium is adjusted so that said reduction occurs substantially instantaneously.

3. The method of claim 2, wherein said rate of incremental introduction of said dicyanoglycol is adjusted so that said reaction medium does not contain more than about 5 percent reaction intermediates.

4. The method of claim 1, wherein said temperature is from about 120°–135° C.

5. The method of claim 1, wherein said pressure is from about 1000–2000 psi.

6. The method of claim 1, wherein the amount of ammonia used is from about 5 to about 30 moles per mole of dicyanoglycol.

7. The method of claim 6, wherein the amount of ammonia is from about 12 to about 20 moles per mole of dicyanoglycol.

8. The method of claim 1, wherein m and n are both at least 1 and not more than about 10; $R_1$ is H; and $R_2$ is selected from H and a lower alkyl group containing from 1 to about 4 carbon atoms.

9. The method of claim 1, wherein said dicyanoglycol is bis-(-2-cyanoethyl)diethylene glycol and said diaminoalkoxy compound is bis-(-3-aminopropyl)diethyleneglycol.

10. The method of claim 1, wherein said dicyanoglycol is bis-(-2-cyanoethyl)ethylene glycol and said diaminoalkoxy compound is bis-(-3-aminopropyl)ethylene glycol.

11. The method of claim 1, wherein said dicyanoglycol is bis-(-2-cyanoethyl)ether and said diaminoalkoxy compound is bis-(-3-aminopropyl)ether.

* * * * *

UNITED STATES PATENT AND TRADEMARK OFFICE
CERTIFICATE OF CORRECTION

PATENT NO. : 4,313,004
DATED : January 26, 1982
INVENTOR(S) : Edward W. Kluger

It is certified that error appears in the above-identified patent and that said Letters Patent is hereby corrected as shown below:

Columns 7 and 8, Table 2, Entry 3, under the caption RXN, PRESSURE (PSI) change "1110-1700" to --1100-1700--.

Signed and Sealed this

Twenty-sixth Day of March 1985

[SEAL]

Attest:

DONALD J. QUIGG

Attesting Officer

Acting Commissioner of Patents and Trademarks